(12) United States Patent
Garai et al.

(10) Patent No.: US 11,904,146 B2
(45) Date of Patent: Feb. 20, 2024

(54) MEDICINE INJECTION DEVICES, SYSTEMS, AND METHODS FOR MEDICINE ADMINISTRATION AND TRACKING

(71) Applicant: Medtronic MiniMed, Inc., Northridge, CA (US)

(72) Inventors: Ellis Garai, Woodland Hills, CA (US); Ashwin K. Rao, West Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 317 days.

(21) Appl. No.: 17/342,449

(22) Filed: Jun. 8, 2021

(65) Prior Publication Data

US 2022/0387723 A1 Dec. 8, 2022

(51) Int. Cl.
*A61M 5/315* (2006.01)

(52) U.S. Cl.
CPC ..... *A61M 5/31568* (2013.01); *A61M 2205/18* (2013.01); *A61M 2205/3306* (2013.01); *A61M 2205/52* (2013.01)

(58) Field of Classification Search
CPC ................ A61M 5/31568; A61M 5/20; A61M 2039/0267; A61M 2039/0276; A61M 2205/3306; A61M 2205/3576
See application file for complete search history.

(56) References Cited

U.S. PATENT DOCUMENTS

| | | | |
|---|---|---|---|
| 4,755,173 A * | 7/1988 | Konopka | .......... A61M 25/0606 604/122 |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A * | 9/1998 | Gross | ................... A61B 5/6848 600/347 |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |

(Continued)

*Primary Examiner* — Tasnim Mehjabin Ahmed

(74) *Attorney, Agent, or Firm* — Carter, DeLuca & Farrell LLP

(57) ABSTRACT

A medicine delivery and tracking system includes a medicine injection pen and a delivery port. The pen includes a needle through which medicine is dispensed and an electronic unit configured to at least one of log dispensing of medicine from the pen, control dispensing of medicine from the pen, or communicate regarding dispensing of medicine from the pen. Alternatively, the electronic unit may be part of a separate computing device. The delivery port is configured for attachment to a user and to receive the needle of the pen such that medicine dispensed from the pen is dispensed into the delivery port and through the delivery port to the user. The delivery port includes a detector mechanism configured to detect a presence of the pen and, in response thereto, to communicate a signal to the electronic unit for use in the at least one of logging, controlling, or communicating.

15 Claims, 14 Drawing Sheets

(56) References Cited

U.S. PATENT DOCUMENTS

| | | |
|---|---|---|
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 * | 11/2012 | Hanson ............... A61M 5/1684 604/67 |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 10,835,727 B2 | 11/2020 | Montalvo et al. |
| 2007/0123819 A1 | 5/2007 | Mernoe et al. |
| 2010/0160861 A1 | 6/2010 | Causey, III et al. |
| 2020/0327973 A1 | 10/2020 | Pryor et al. |

\* cited by examiner

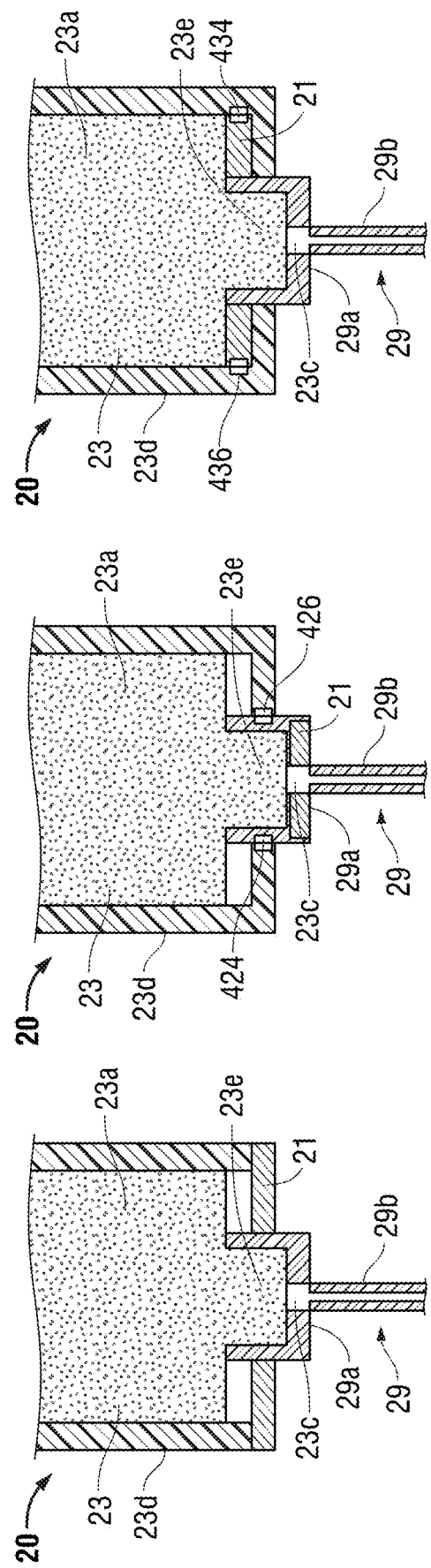

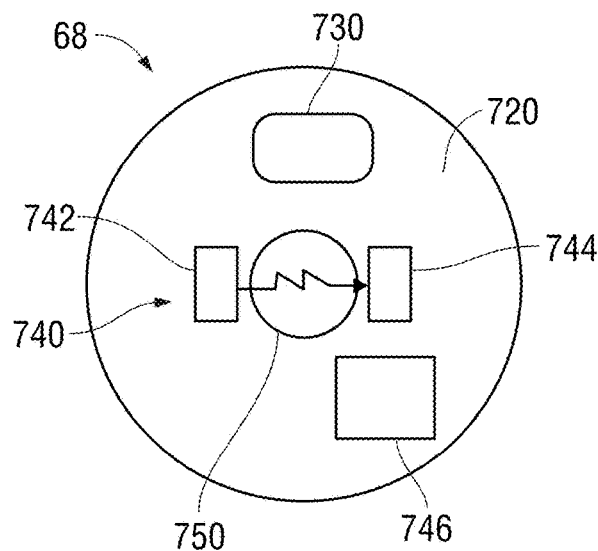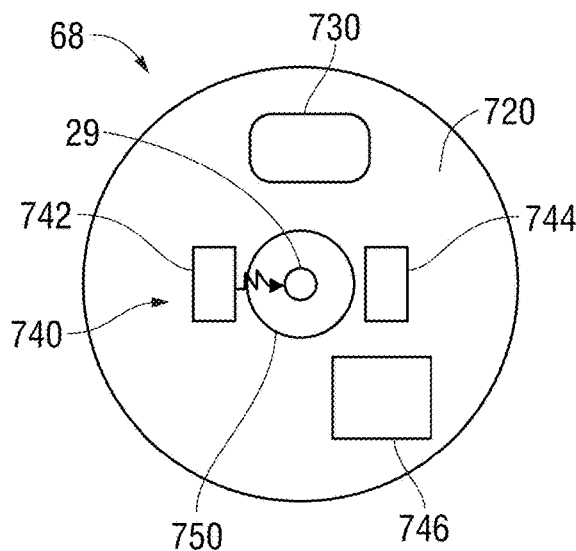
FIG. 8A  FIG. 8B
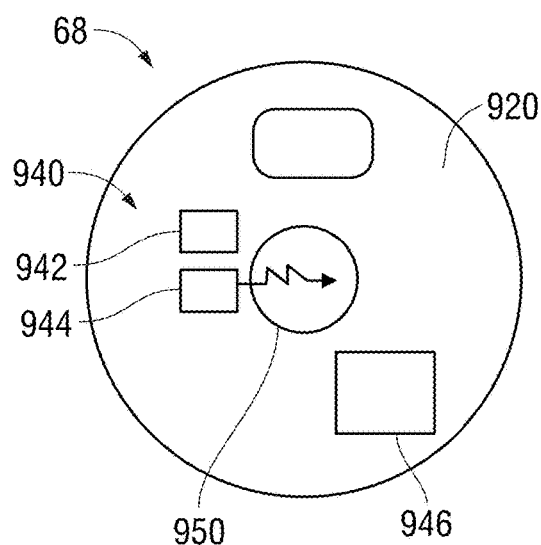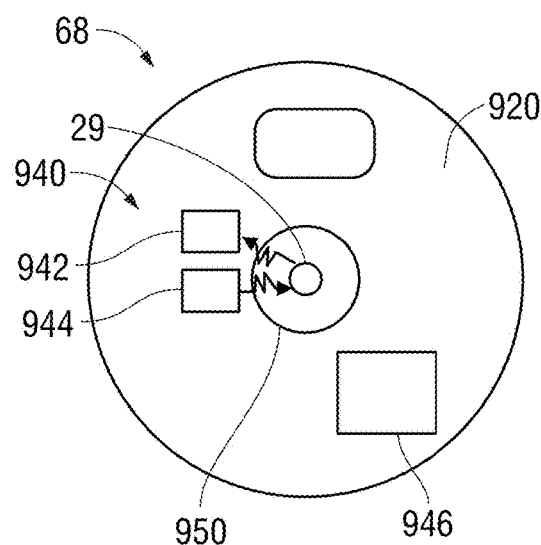
FIG. 9A  FIG. 9B

MEDICINE INJECTION DEVICES, SYSTEMS, AND METHODS FOR MEDICINE ADMINISTRATION AND TRACKING

FIELD

The present disclosure relates to medicine injection devices, systems, and methods for medicine administration and tracking.

BACKGROUND

Diabetes mellitus ("diabetes") is a metabolic disease associated with high blood sugar due to insufficient production or use of insulin by the body. Diabetes affects hundreds of millions of people and is among the leading causes of death globally. Diabetes has been categorized into three types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. Gestational diabetes can occur during pregnancy when a pregnant woman develops a high blood glucose level. Gestational diabetes often resolves after pregnancy; however, in some cases, gestational diabetes develops into type 2 diabetes.

Various diseases and medical conditions, such as diabetes, require a user to self-administer doses of medicine. When administering a liquid medicine by injection, for example, the appropriate dose amount is set and then dispensed by the user, e.g., using a syringe, a medicine delivery pen, or a pump. Regardless of the particular device utilized for injecting the liquid medicine, it is important to accurately track the medicine dosed, particularly for managing lifelong or chronic conditions like diabetes.

SUMMARY

To the extent consistent, any of the aspects and features detailed herein can be utilized with any of the other aspects and features detailed herein in any suitable combination.

Provided in accordance with aspects of the present disclosure is a medicine delivery and tracking system including a medicine injection pen including a needle through which medicine is dispensed from the pen and an electronic unit configured to at least one of log dispensing of medicine from the pen, control dispensing of medicine from the pen, or communicate regarding dispensing of medicine from the pen. Alternatively or additionally, the electronic unit or another electronic unit may be part of a separate computing device configured to perform the at least one of logging, controlling, or communicating. The system further includes a delivery port configured for attachment to a user and to receive the needle of the pen such that medicine dispensed from the pen is dispensed into the delivery port and through the delivery port to the user, wherein the delivery port includes a detector mechanism configured to detect a presence of the pen and, in response thereto, to communicate a signal to the electronic unit of the pen for use in the at least one of logging, controlling, or communicating.

In an aspect of the present disclosure, the detector mechanism includes an optical detector configured to optically detect the presence of the needle of the pen within the delivery port.

In another aspect of the present disclosure, the detector mechanism includes a switch configured for physical actuation by the pen to detect the presence of the pen.

In still another aspect of the present disclosure, the detector mechanism includes a contact assembly configured to detect the presence of the pen based on the needle of the pen establishing or breaking an electrical connection of the contact assembly.

In yet another aspect of the present disclosure, the signal communicated from the detector mechanism of the delivery port to the electronic unit(s) instructs the electronic unit(s) to control the dispensing of medicine from the pen by permitting or inhibiting actuation of the pen.

In still yet another aspect of the present disclosure, the signal communicated from the detector mechanism of the delivery port to the electronic unit(s) instructs the electronic unit(s) to log a dispensing event only when the detector mechanism detects the presence of the pen.

In another aspect of the present disclosure, the signal communicated from the detector mechanism of the delivery port to the electronic unit(s) instructs the electronic unit(s) to communicate an alert regarding whether dispensing of medicine from the pen is recommended or not recommended.

A method of medicine delivery and tracking provided in accordance with the present disclosure includes activating a detector mechanism of a delivery port installed on a user and determining, using the detector mechanism, whether a medicine injection pen is inserted into the delivery port. In a case where it is determined that the pen is inserted into the delivery port, the method further includes at least one of enabling medicine delivery from the pen to the delivery port, initiating delivery of medicine from the pen to the delivery port, or providing an alert indicating that medicine can be delivered from the pen to the delivery port. In a case where it is not determined that the pen is inserted into the delivery port, the method further includes at least one of inhibiting medicine delivery from the pen to the delivery port or providing an alert indicating that medicine should not be delivered from the pen to the delivery port.

In an aspect of the present disclosure, in a case where it is determined that the pen is inserted into the delivery port, the method further includes determining whether there is a delivery error during delivery of medicine from the pen to the delivery port. In a case where it is determined that there is an error, the method further includes at least one of inhibiting further medicine delivery from the pen to the delivery port or providing an alert indicating that further delivery of medicine from the pen to the delivery port should be stopped. In a case where it is determined that there is not an error, the method further includes confirming completion of medicine delivery from the pen to the delivery port.

In another aspect of the present disclosure, in the case where it is determined that the pen is inserted into the delivery port, the method further includes, prior to the at least one of enabling, initiating, or providing, determining whether medicine delivery is safe based on prior medicine delivery data. In a case where medicine delivery is determined not to be safe, the method further includes at least one of inhibiting medicine delivery from the pen to the delivery port or providing an alert indicating that medicine should not be delivered from the pen to the delivery port. In a case where medicine delivery is determined to be safe, the method further includes proceeding with the at least one of enabling, initiating, or providing.

In yet another aspect of the present disclosure, the detector mechanism is configured to communicate with the pen for the at least one of enabling, initiating, or providing, and for the at least one of inhibiting or providing.

In still another aspect of the present disclosure, the detector mechanism is configured to communicate with the pen or with a computing device for the at least one of enabling, initiating, or providing, and for the at least one of inhibiting or providing.

BRIEF DESCRIPTION OF DRAWINGS

FIGS. 4A-4C are enlarged, longitudinal, cross-sectional views of various different configurations of the dispensing end of medicine injection pen of FIG. 1A in accordance with the present disclosure;

FIGS. 8A and 8B are bottom views of a detector module configured for use with the delivery port of FIG. 1A with and without a needle of the medicine injection pen received therethrough;

FIGS. 9A and 9B are bottom views of another detector module configured for use with the delivery port of FIG. 1A with and without a needle of the medicine injection pen received therethrough;

DETAILED DESCRIPTION

Figure 1A:
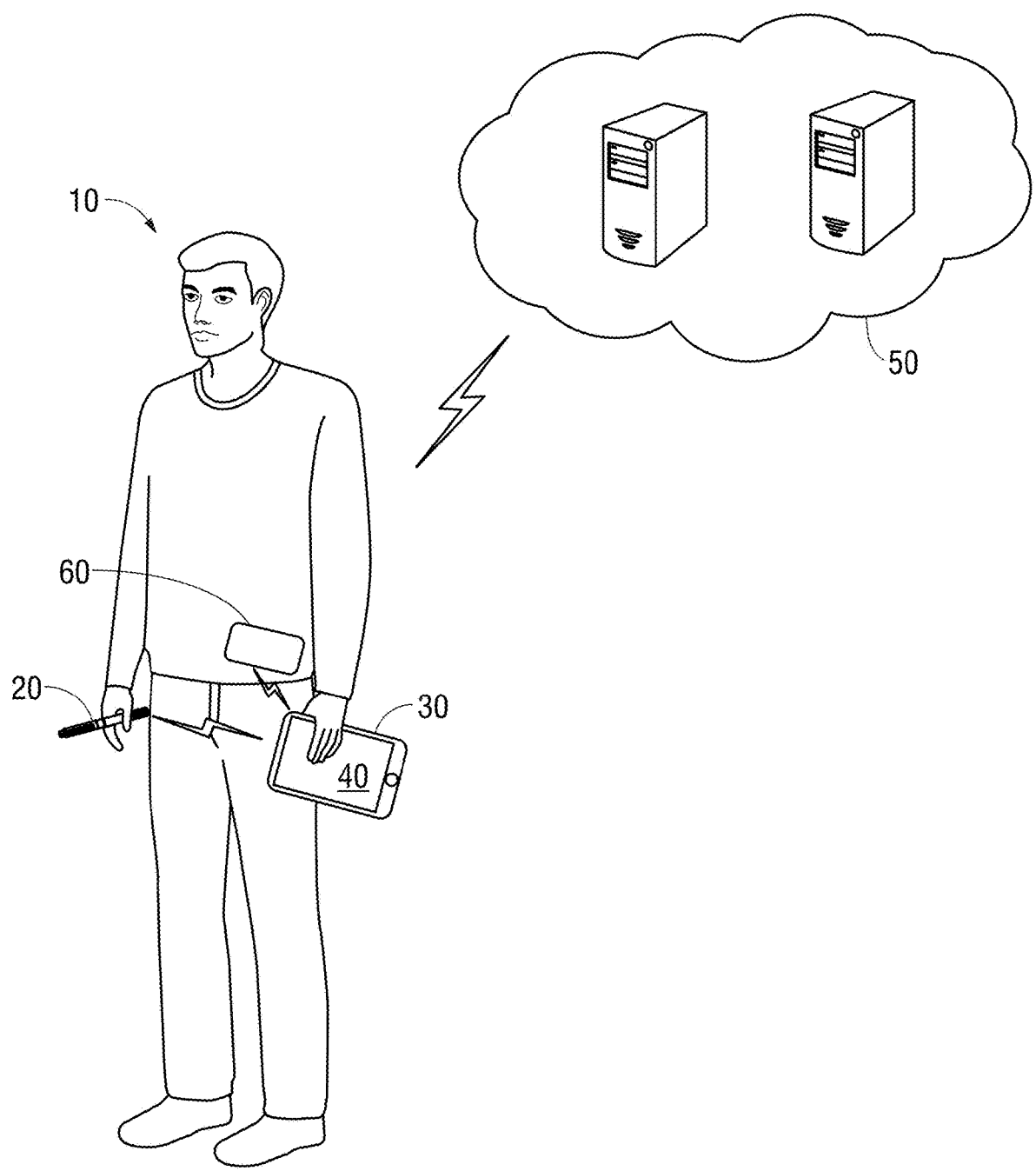
FIG. 1A is a schematic illustration of a medicine administration and tracking system provided in accordance with the present disclosure including a medicine injection pen, a computing device, a delivery port, and, in aspects, a data processing system.

FIG. 1A illustrates a medicine administration and tracking system 10 provided in accordance with the present disclosure including a medicine injection pen 20, a computing device 30 running a health management application 40, and a delivery port 60. Pen 20 and delivery port 60 are configured for selective communication with one another and computing device 30 is configured for wireless communication with pen 20 and/or delivery port 60. System 10 may further include, in aspects, other devices that are part of or connected to system 10 such as, for example, a data processing system 50 and/or a sensor device (not shown). While the present disclosure is detailed herein with respect to medicine injection pen 20 and delivery port 60 of system 10 for diabetes management, it is understood that other suitable injection devices and/or delivery devices may be utilized in accordance with the present disclosure, that the present disclosure is also applicable to management of other diseases and medical conditions and/or that the present disclosure is also capable of use with other medicine administration and tracking systems.

Medicine injection pen 20, described in greater detail below, is a reusable device configured to removably receive a medicine cartridge, e.g., a cartridge of insulin, for injecting a selected dose of insulin into a user and recording information concerning the injected dose of insulin, e.g., a dose amount and/or timestamp data associated with the dose. Medicine injection pen 20 may alternatively be configured as a disposable device including an integrated medicine cartridge whereby the entire device is discarded after the insulin cartridge is expended. In other aspects, medicine injection pen 20 is replaced with any other suitable medicine injection device such as, for example, a syringe, pump, cannula, etc.

Computing device 30 is detailed and illustrated herein as a smartphone, although any other suitable computing device may be provided such as, for example, a tablet, a wearable computing device (e.g., a smart watch, smart glasses, etc.), a laptop and/or desktop computer, a smart television, a network-based server computer, etc.

Health management application 40 is paired with pen 20, which may be a prescription-only medical device, via smartphone 30, although other suitable configurations are also contemplated. In aspects, the pairing of smartphone 30 with pen 20 at least partially unlocks health management application 40 to enable the user to utilize some or all features of health management application 40, e.g., according to the user's prescription. Thus, the act of pairing can unlock and enable the functionality of health management application 40 and/or system 10 (including pen 20), while health management application 40 (and/or system 10) may provide only limited features in the absence of pairing with pen 20. Health management application 40 may, in aspects, be paired with delivery port 60 and/or pen 20 may be paired with delivery port 60 in a manner similar to the pairing detailed above.

Health management application 40 of smartphone 30, in aspects, can monitor and/or control functionalities of pen 20 and provide a dose calculator module and/or decision support module that can calculate and recommend a dose of medicine for the user to administer using pen 20. Health management application 40 provides a user interface, on the user interface of smartphone 30, to allow a user to manage health-related data. For example, health management application 40 can be configured to control some functionalities of pen 20 and/or to provide an interactive user interface to allow a user to manage settings of pen 20 and/or settings for smartphone 30 that can affect the functionality of system 10 (FIG. 1A). Smartphone 30 can additionally or alternatively be used to obtain, process, and/or display contextual data that can be used to relate to the health condition of the user, including the condition for which pen 20 is used to treat. For example, smartphone 30 may be operable to track the location of the user; physical activity of the user including step count, movement distance and/or intensity, estimated calories burned, and/or activity duration; and/or interaction pattern of the user with smartphone 30. In aspects, health management application 40 can aggregate and process the contextual data to generate decision support outputs, e.g., on the user interface, to guide and aid the user in monitoring their condition, using pen 20, and/or managing their behavior to promote treatment and better health outcomes.

In aspects, system 10 further includes a data processing system 50 in communication with pen 20, delivery port 60, and/or smartphone 30. Data processing system 50 can include one or more computing devices in a computer system and/or communication network accessible via the internet, e.g., including servers and/or databases in the cloud. System 10 can additionally or alternatively include a sensor device (not shown) to monitor one or more health metrics and/or physiological parameters of the user. Examples of health metric and physiological parameter data monitored by the sensor device include analytes (e.g., glucose), heart rate, blood pressure, user movement, temperature, etc. The sensor device may be a wearable sensor device such as a continuous glucose monitor (CGM) to obtain transcutaneous or blood glucose measurements that are processed to produce continuous glucose values. For example, the CGM can include a glucose processing module implemented on a stand-alone display device and/or implemented on smartphone 30, which processes, stores, and displays the continuous glucose values for the user. Such continuous glucose values can be utilized by health management application 40, for example, for displaying health data, in dose calculation and/or decision support, etc. In aspects, the sensor device is incorporated into delivery port 60 such that delivery port 60, in addition to facilitating deliver of medicine to the user, also functions to sense health metric(s) and/or physiological parameter(s). For example, and without limitation, delivery port 60 may incorporate a CGM.

Figure 1B:
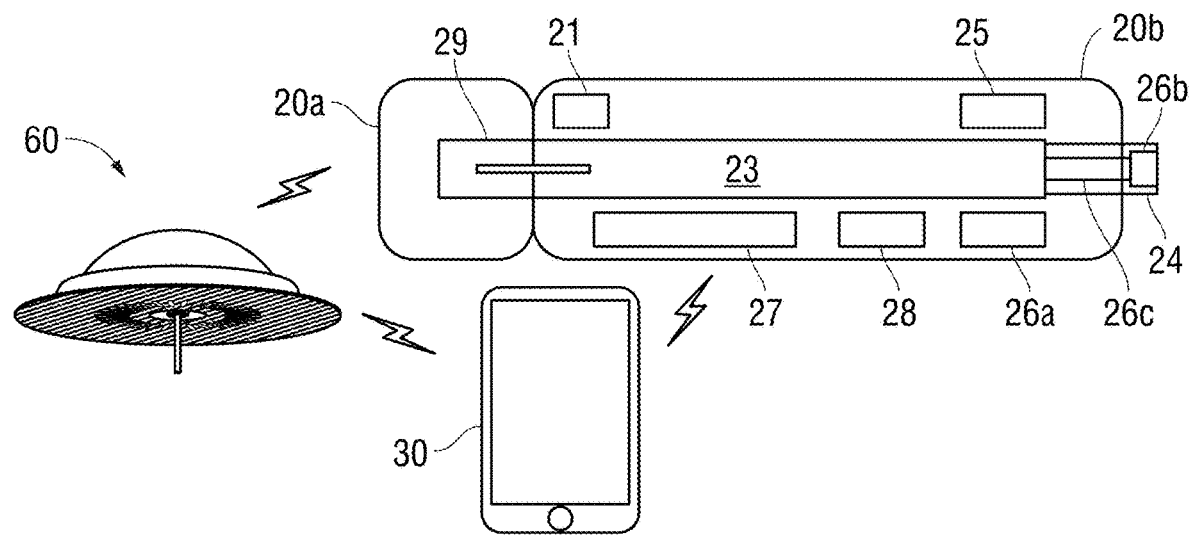
FIG. 1B illustrates the medicine injection pen, delivery port, and computing device of the system of FIG. 1A operably communicating with one another, wherein the medicine injection pen is shown diagrammatically to illustrate the components thereof.

With reference to FIG. 1B, pen 20 includes a cap 20a configured to protect a medicine dispensing element (e.g., a needle 29) and a body 20b configured to contain a replaceable medicine cartridge 23, e.g., an insulin cartridge. Pen 20 further includes a dose dispensing mechanism 24 to dispense (e.g., deliver) medicine contained in medicine cartridge 23 out of pen 20 (e.g., through needle 29); a dose setting mechanism 25 to enable the selection and/or setting of a dose of medicine to be dispensed; an operations monitoring mechanism 28 (e.g., including one or more switches, sensors (electrical, optical, acoustic, magnetic, etc.), encoders, etc.) to qualitatively determine that pen 20 is being operated and/or to monitor the operation of pen 20 (e.g., to quantitatively determine an amount of medicine set and/or dosed); an electronics unit 27 that can include a processor, a memory, a transceiver, and a battery or other suitable power source; and a port interface mechanism 21 configured to operably interface with delivery port 60, as detailed below.

In aspects, in order to operate pen 20, the user removes cap 20a and sets e.g., dials, a dose using a dose knob 26a of dose setting mechanism 25. For example, the dose may be adjusted up or down to achieve a desired dose amount prior to administration of the dose by rotating dose knob 26a in an appropriate direction. Once the appropriate dose has been set, the user applies a force against a dose dispensing button 26b of dose dispensing mechanism 24 to begin dispensing. More specifically, to begin dispensing, the user presses against the portion of dose dispensing button 26b that protrudes from body 20b of pen 20 to thereby drive a driving element 26c, e.g., a drive screw 26c, of dose dispensing mechanism 24 against an abutment, e.g., piston 23b (FIG. 2B), of medicine cartridge 23 to dispense an amount of medicine from cartridge 23 through needle 29 into the user in accordance with the dose amount set by dose setting mechanism 25, e.g., dose knob 26a, during setting.

Operations monitoring mechanism 28 of pen 20 senses movement of a rotating and/or translating driving component (e.g., drive screw 26c (see also FIG. 2B)) of dose dispensing mechanism 24. Operations monitoring mechanism 28 may include one or more switches, sensors, and/or encoders for this purpose. More specifically, any suitable switch(es), sensor(s), and/or encoder(s) may be utilized to sense rotary and/or linear movement. Non-limiting examples of such include rotary and linear encoders, Hall effect and other magnetic-based sensors, linearly variable displacement transducers, optical sensors, etc. With respect to an encoder, for example, the encoder can be configured to sense the rotation of drive screw 26c (FIG. 2B) that, in turn, translates to dispense medicine; thus, by sensing rotation of drive screw 26c (FIG. 2B), the translational movement of drive screw 26c can be readily determined. Movement of the encoder may be detected as data processed by the processor of electronics unit 27 of pen 20, from which the amount of medicine dosed can be determined.

In aspects, the processor of electronics unit 27 of pen 20 can store the dose along with a timestamp for that dose and/or any other information associated with the dose. In aspects, the transceiver of electronics unit 27 enables pen 20 to transmit the dose and related information to smartphone 30. In such aspects, once the dose is transmitted, the dose data and any related information associated with that particular transmitted dose is marked in the memory of electronics unit 27 of pen 20 as transmitted. If the dose is not yet transmitted to smartphone 30 such as, for example, because no connection between the pen 20 and smartphone 30 is available, then the dose and associated data can be saved and transmitted the next time a successful communication link between pen 20 and smartphone 30 is established.

The timestamp may be the current time or a time from a count-up timer. When the dose and associated information is communicated to health management application 40 running on smartphone 30, the timestamp and/or "time-since-dose" parameter (as determined by the count-up timer) is transmitted by pen 20 and received by smartphone 30 for storage in memory 33 of data processing unit 31 of the smartphone 30 (see FIG. 1C). Where a count-up timer is utilized, the time of the dose can be determined without pen 20 having to know the current time, which can simplify operation and setup of pen 20. That is, health management application 40 can determined the time of dose based on the current time and the value returned from the count-up timer.

Dose dispensing mechanism 24 of pen 20 can include a manually powered mechanism (user powered and/or mechanically biased), a motorized mechanism, or an assisted mechanism (e.g., a mechanism that operates partly on manual power and partly on motorized power). Regardless of the particular configuration of the dose dispensing mechanism 24, as noted above, when a force (e.g., a manual force, electrically-powered motor force, or combinations thereof) is applied to drive screw 26c of dose dispensing mechanism 24, drive screw 26c turn provides a force to urge medicine from medicine cartridge 23 to deliver the set or dialed dose. In aspects, dose dispensing mechanism 24 can be operated such that rotation and/or translation of the driving element, e.g., drive screw 26c, is facilitated by a variable tension spring or a variable speed motor to inject the dose over a specific time frame (e.g., 1 s, 5 s, etc.) to help reduce the pain of dosing and/or for other purposes.

Port interface mechanism 21 is configured to electrically and/or mechanically interface with delivery port 60 when pen 20 is sufficiently approximated relative to delivery port 60. Port interface mechanism 21, more specifically, may electrically interface with delivery port 60 via a physical connection (e.g., one or more pairs of mating contacts on pen 20 and delivery port 60 that connect upon sufficient approximation of pen 20 relative to delivery port 60) and/or via a contactless connection (e.g., via Near Field Communication (NFC), optical (such as, for example, infrared), Radio Frequency Identification (RFID), or in any other suitable manner). Power, data, and/or control signals may be communicated between port interface mechanism 21 of pen 20 and delivery port 60 via the electrical interface. The mechanical interface between port interface mechanism 21 of pen 20 and delivery port 60 may activate a physical switch or other mechanical component, facilitate mechanical alignment of pen 20 relative to delivery port 60, releasably secure pen 20 relative to delivery port 60, etc.

Figure 1C:
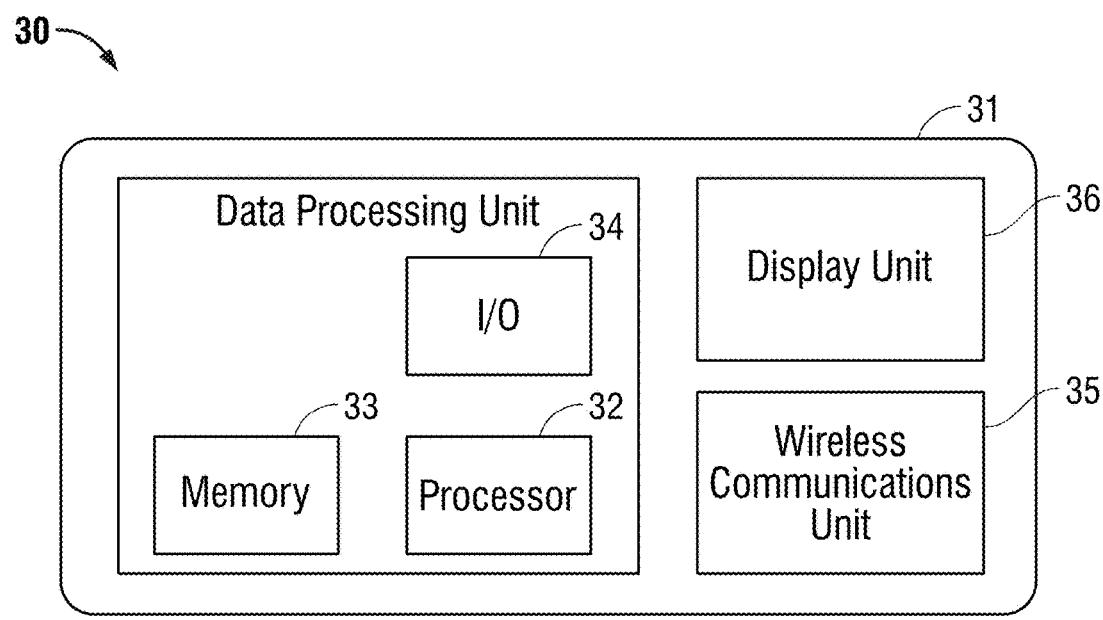
FIG. 1C is a block diagram of the computing device of the system of FIG. 1A.

FIG. 1C illustrates smartphone 30 of system 10 (FIG. 1A) including a data processing unit 31, a wireless communications unit 35, and a display unit 36. Data processing unit 31 includes a processor 32 to process data, a memory 33 in communication with the processor 32 to store data, and an input/output unit (I/O) 34 to interface processor 32 and/or memory 33 to other modules, units, and/or devices of smartphone 30 and/or external devices. Processor 32 can include a central processing unit (CPU) or a microcontroller unit (MCU). Memory 33 can include and store processor-executable code, which when executed by processor 32, configures the data processing unit 31 to perform various operations, e.g., such as receiving information, commands, and/or data, processing information and data, and transmitting or providing information/data to another device. In aspects, data processing unit 31 can transmit raw or processed data to data processing system 50 (FIG. 1A). To support various functions of data processing unit 31, memory 33 can store information and data, such as instructions, software, values, images, and other data processed or referenced by processor 32. For example, various types of Random Access Memory (RAM) devices, Read Only Memory (ROM) devices, Flash Memory devices, and other suitable storage media can be used to implement storage functions of memory 33. I/O 34 of data processing unit 31 can interface data processing unit 31 with wireless communications unit 35 to utilize various types of wired or wireless interfaces compatible with typical data communication standards, for example, which can be used in communications of data processing unit 31 with other devices such as pen 20, via a wireless transmitter/receiver (Tx/Rx), e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. I/O 34 of data processing unit 31 can also interface with other external interfaces, sources of data storage, and/or visual or audio display devices, etc. to retrieve and transfer data and information that can be processed by processor 32, stored in memory 33, and/or exhibited on an output unit of smartphone 30 and/or an external device. For example, display unit 36 of smartphone 30 can be configured to be in data communication with data processing unit 31, e.g., via I/O 34, to provide a visual display, an audio display, and/or other sensory display that produces the user interface of the health management application 40 (FIG. 1A). In some examples, display unit 36 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Once smartphone 30 receives the dose and related information (e.g., which can include time information, dose setting, and/or dose dispensing information, and other information about pen 20 and/or the environment as it relates to a dosing event), smartphone 30 stores the dose related information in memory 33, e.g., which can be included among a list of doses or dosing events. In aspects, via the user interface associated with health management application 40, smartphone 30 allows the user to browse a list of previous doses, to view an estimate of current medicine active in the user's body (medicine on board, e.g., insulin on board) based on calculations performed by health management application 40, and/or to utilize a dose calculation module to assist the user regarding dose setting information on the size of the next dose(s) to be delivered. For example, the user may enter carbohydrates to be eaten and current blood sugar (which alternatively may be obtained directly from the sensor device, and health management application 40 may already know insulin on board. Using these parameters, a suggested medicine dose (e.g., a recommended insulin dose), calculated by the dose determination module, may be determined. In aspects, smartphone 30 can also allow the user to manually enter dose data, e.g., boluses, which may be useful if the battery in pen 20 has been depleted or another medicine delivery device, e.g., a syringe, was utilized to dose.

Figure 2A:
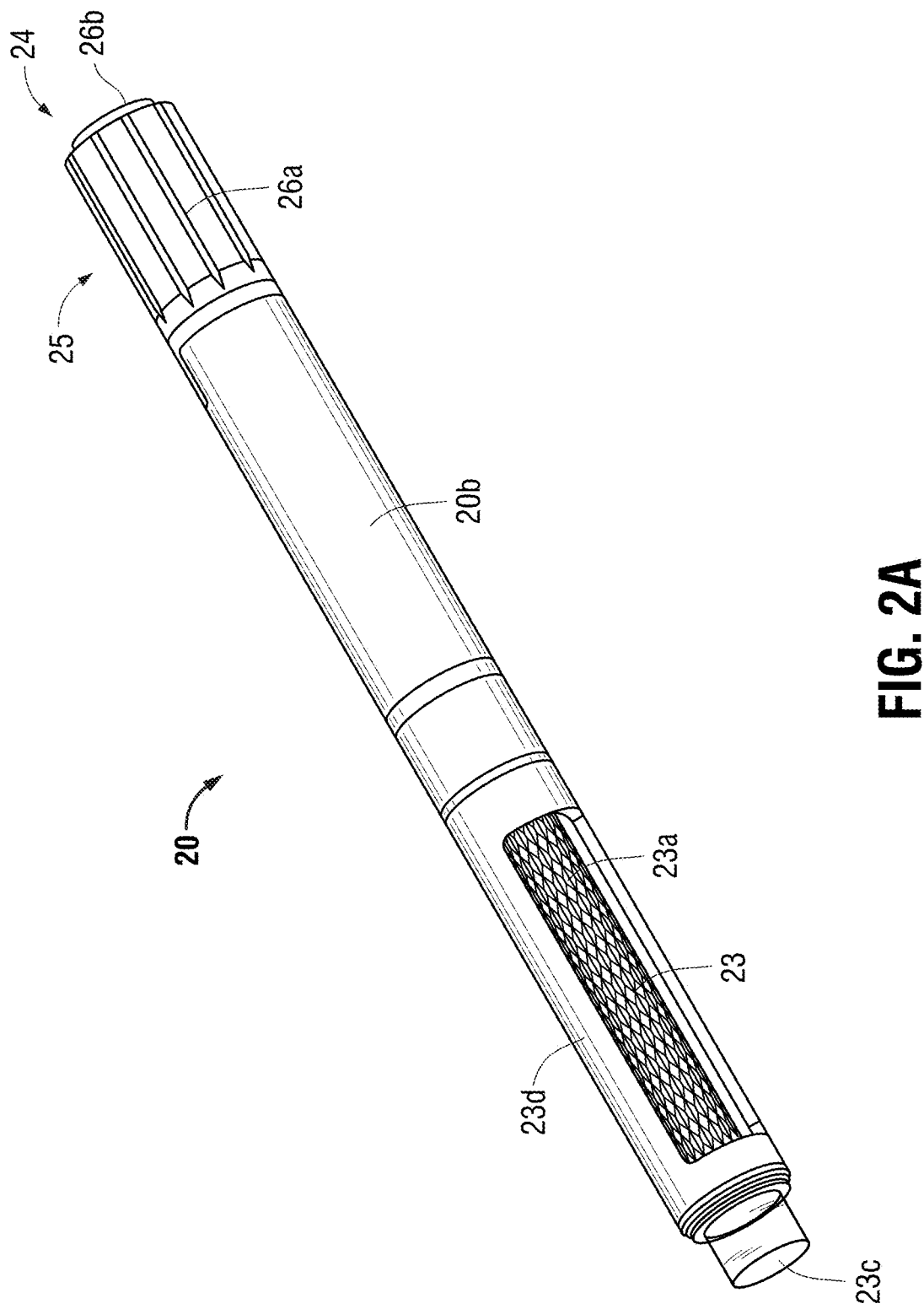
FIGS. 2A and 2B are perspective and longitudinal, cross-sectional views, respectively, of the medicine injection pen of FIG. 1A.
Figure 2B:
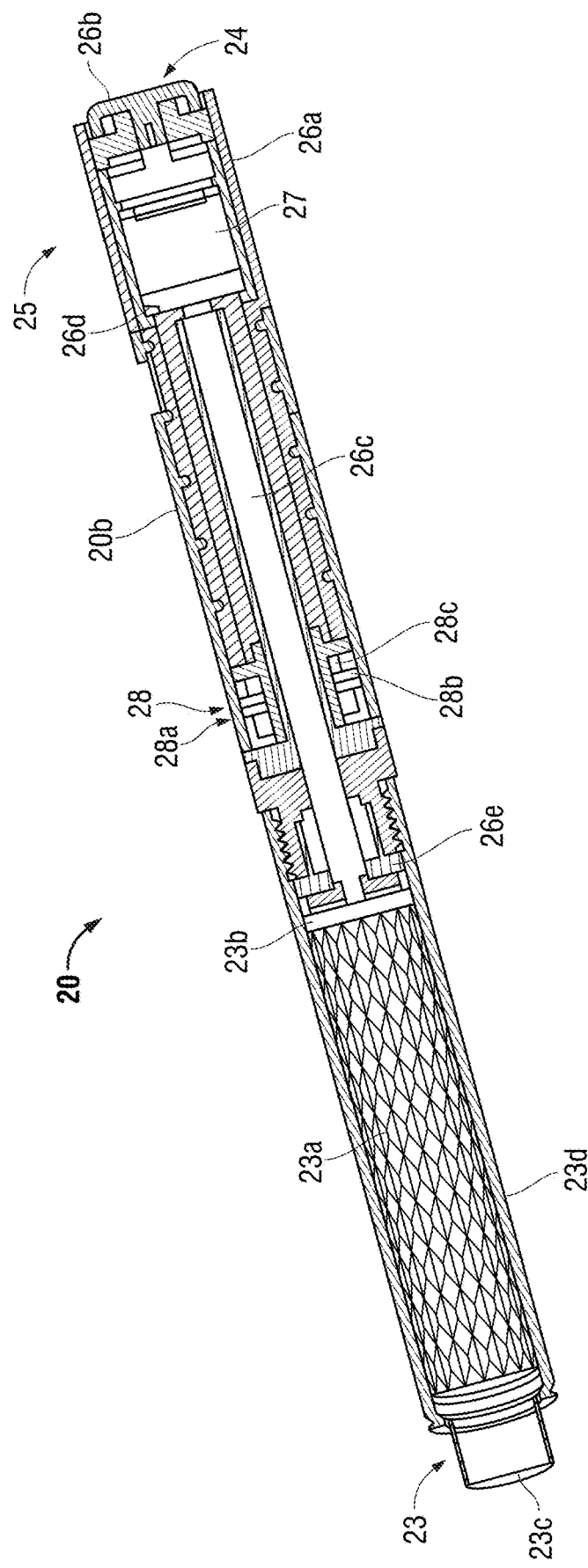

Referring to FIGS. 2A and 2B, pen 20 and, in particular, the mechanical and hardware features thereof, is detailed, although other mechanical and hardware configurations of pen 20 are also contemplated. Pen 20 is shown configured as a reusable device for use with replaceable medicine cartridge 23 which, once emptied (or for other purposes), can be replaced with another medicine cartridge 23 or refilled and reinstalled for subsequent use. Medicine cartridge 23 includes a vial body 23a defining an interior volume configured to retain a volume of medicine, e.g., insulin, therein, and a piston 23b sealingly and slidingly disposed within vial body 23a such that displacement of piston 23b within vial body 23a towards the dispensing end of vial body 23a forces medicine from the interior volume through dispensing opening 23c of cartridge 23 and needle 29 (FIG. 1B) for injection into the user.

Medicine cartridge 23 is held within a cartridge housing 23d of pen 20 and, in aspects, may be seated within a corresponding cartridge adapted (not shown) positionable within cartridge housing 23d to enable use of various different medicine cartridges (e.g., of different size, shape, manufacturer, etc.) with pen 20. Cartridge housing 23d is releasably engageable with body 20b of pen 20, e.g., via threaded engagement, such that, when cartridge housing 23d is disengaged from body 20b of pen 20, medicine cartridge 23 can be removed and replaced and such that, when cartridge housing 23d is engaged with body 20b of pen 20 with a medicine cartridge 23 therein, medicine cartridge 23 is operably positioned relative to dose dispensing mechanism 24 of pen 20. However, other suitable configurations enabling removal and replacement of a medicine cartridge 23 are also contemplated.

Continuing with reference to FIGS. 2A and 2B, dose knob 26a of pen 20 may be coupled to body 20b of pen 20 in threaded engagement via corresponding threads defined on an exterior surface of a portion of dose knob 26a and an interior surface of a portion of body 20b. In aspects, electronics unit 27 may reside within an electronics housing disposed or defined within dose knob 26a and be coupled thereto via a locking mechanism 26d (e.g., a catch-protrusion mechanism, a clutch, etc.) such that, when dose knob 26a is rotated into or out of body 20b to select or adjust the dose to be injected, electronics unit 27 remains stationary (e.g., wherein the locking mechanism 26d is in an unlocked state); however, when dispensing button 26b is actuated, locking mechanism 26d is engaged to lock electronics unit 27 and dose knob 26a to one another such that electronics unit 27 and dose knob 26a rotate together as they translate into body 20b upon actuation of dose dispensing mechanism 24 to inject the selected dose.

Figure 3A:
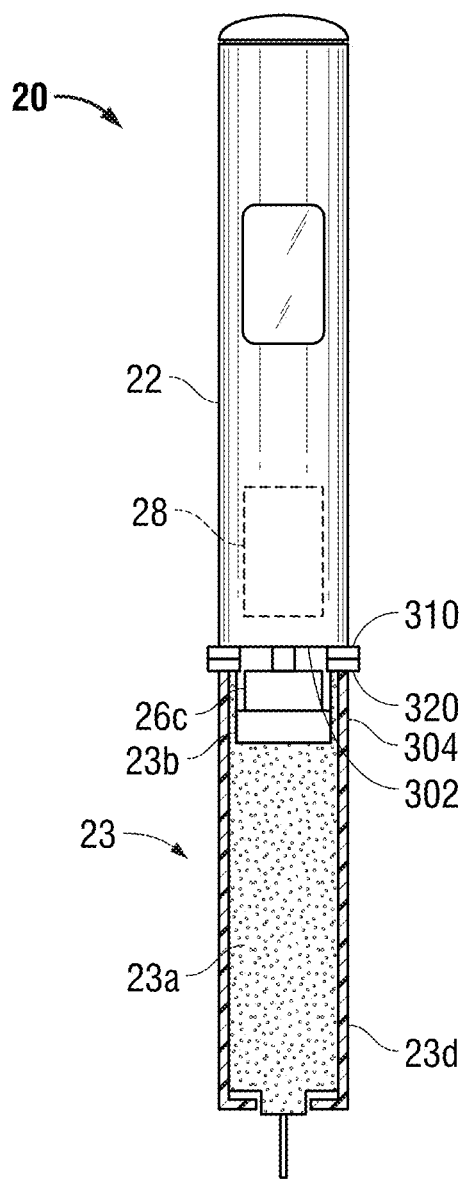
FIGS. 3A and 3B are side, partial longitudinal, cross-sectional views of the medicine injection pen of FIG. 1A with the medicine cartridge in a full condition and the medicine cartridge in a partially emptied condition, respectively.
Figure 3B:
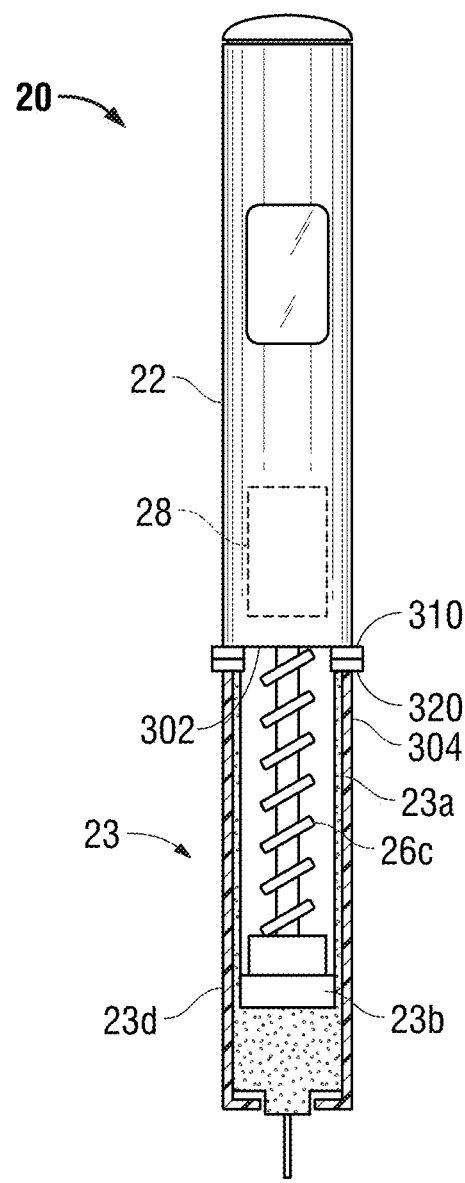
Figure 5A:
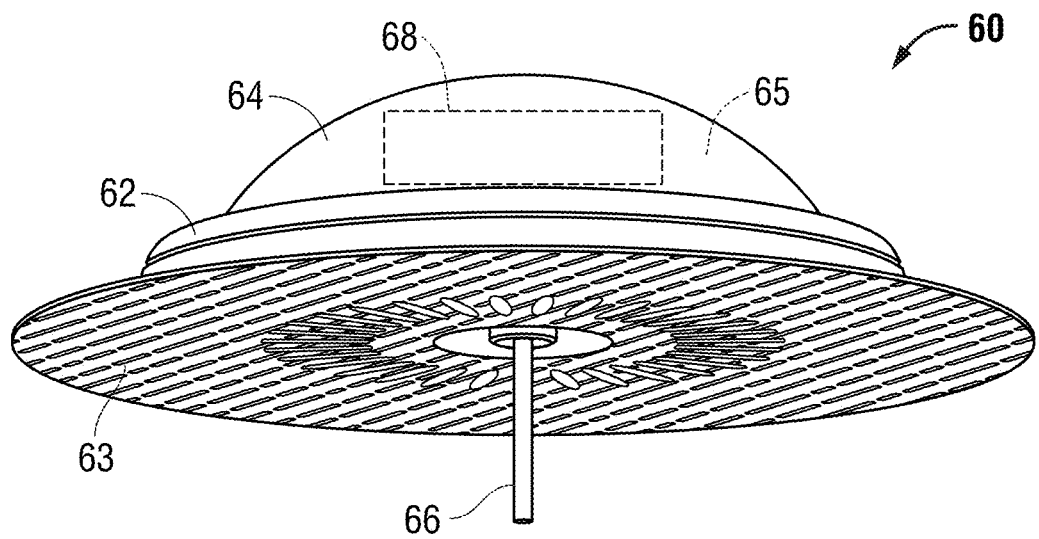
FIGS. 5A and 5B are perspective and top views, respectively, of the delivery port of FIG. 1A.
Figure 5B:
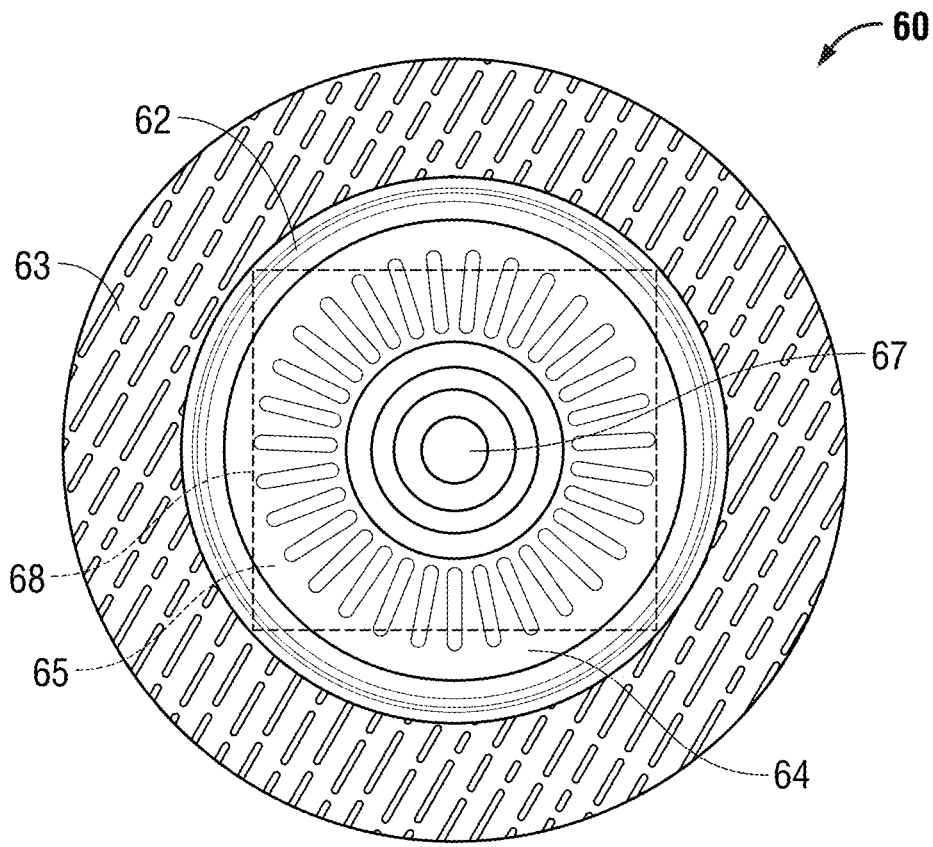

With additional reference to FIGS. 3A and 3B, the rotation of the dose knob 26a (and electronics unit 27) during actuation drives (direct or indirect) rotation of drive screw 26c which rides within a nut 26e which is fixed to body 20b of pen 20. In this manner, rotation of drive screw 26c also results in translation of drive screw 26c (due to the pitched threading of drive screw 26c) towards medicine cartridge 23 to thereby drive piston 23b through vial body 23a to expel medicine from medicine cartridge 23 for injection into the user. The extent to which dose knob 26a extends from body 20b of pen 20 prior to actuation (which corresponds to the selected dose to be injected) defines the maximum amount of rotation of dose knob 26a and, thus, drive screw 26c during actuation; as such, the amount of medicine expelled from medicine cartridge 23 during actuation cannot exceed the selected dose amount.

Operations monitoring mechanism 28 of pen 20 may include a rotary encoder 28a having a first part 28b rotationally fixed relative to body 20b of pen 20 and a second part 28c rotationally fixed relative to drive screw 26c such that relative rotation between the first and second parts 28b, 28c (which, in turn, is indicative of rotation of drive screw 26c relative to body 20b during dose dispensing), can be sensed and, thus, from which an amount of medicine dispensed can be determined (due to the proportional relationship between rotation of drive screw 26c and translation of piston 23b). Alternatively or additionally, rotary encoder 28a may be configured to sense the amount of medicine dialed for dosing. In aspects, rotary encoder 28a is an electrical contact encoder including one or more contacts disposed on one of the parts 28b, 28c and a code wheel disposed on the other part 28b, 28c, although other configurations and/or types of encoders are also contemplated. Regardless of the particular type of encoder or other sensory components of operations monitoring mechanism 28, relative motion is measured and transmitted to electronics unit 27 for processing (e.g., determining an amount of medicine dispensed), storage (e.g., storing in memory the amount of medicine dispensed together with timestamp data) and/or transmission (e.g., transmitting the stored data to smartphone 30).

Continuing with reference to FIGS. 3A and 3B, in aspects, pen 20 may include one or more contacts 310, e.g., one or more ring contacts or spaced-apart contacts, disposed on the outer periphery of body 20b of pen 20 adjacent an engagement face 302 thereof or on engagement face 302. Engagement face 302 is configured to mate with a corresponding engagement face 304 of cartridge housing 23d upon engagement, e.g., threaded engagement, of cartridge housing 23d with body 20b of pen 20. Cartridge housing 23d includes one or more contacts 320, e.g., one or more ring contacts or spaced-apart contacts, disposed on or adjacent engagement face 304. In this manner, upon engagement of cartridge housing 23d with body 20b of pen 20, contacts 310, 320 connect with one another to enable electrical communication therebetween, e.g., of power signals, control signals, data signals, sensor signals, etc. In aspects where electrical communication between cartridge housing 23d and body 20b is not required or is provided in another manner, e.g., wirelessly, contacts 310, 320 may be omitted.

Referring to FIGS. 4A-4C, as noted above, pen 20 includes a port interface mechanism 21 configured to electrically and/or mechanically interface with delivery port 60 (FIG. 1A) when pen 20 is sufficiently approximated relative to delivery port 60 (FIG. 1A). With respect to electrical interfacing, port interface mechanism 21 may be configured to electrically connect with delivery port 60 via a physical and/or a contactless connection to enable transmission of power, data, and/or control signals between port interface mechanism 21 of pen 20 and delivery port 60. More specifically, although operations monitoring mechanism 28 (FIGS. 2B-3B) enables determination of the amount of medicine dispensed based on the rotation of drive screw 26c (FIG. 3B), operations monitoring mechanism 28 (FIGS. 2B-3B) itself cannot determine the result of the dispensing event, e.g., whether the dispensed medicine was properly delivered to the user, whether the dispensing event was a priming event, etc. That is, while the amount of medicine dispensed can be readily determined using rotary encoder 28a (FIG. 2B) (or other suitable sensor), the amount of medicine delivered to the user cannot necessarily be determined without additional processing, assumptions, and/or data input. FIGS. 4A-4C provide various configurations of port interface mechanism 21 of pen 20 that enable communication with delivery port 60 (FIG. 1A) to provide such additional processing, assumptions, and/or data input to enable determination of not only the amount of medicine dispensed from pen 20, but also the type of dispensing event and/or whether the dispensed medicine was properly delivered to the user.

Turning to FIGS. 4A-4C, a neck 23e extends from the dispensing end of vial body 23a of medicine cartridge 23 through an opening at the dispensing end of cartridge housing 23d. Thus, neck 23e is at least partially exposed to enable releasable attachment of needle 29 thereto, e.g., via threaded engagement. In other configurations, needle 29 is permanently affixed to cartridge housing 23d or vial body 23a.

Needle 29 includes a needle hub 29a configured to releasably engage neck 23e and a hollow needle body 29b configured for insertion into delivery port 60 (FIG. 1A) or a user's skin to deliver medicine therethrough into the user's body. Upon engagement of needle hub 29a with neck 23e, dispensing opening 23c of vial body 23a is disposed in fluid communication with hollow needle body 29b to enable the delivery of medicine therethrough upon actuation of pen 20. In preparation for injection, hollow needle body 29b of needle 29 is inserted into delivery port 60 (FIG. 1A) or pierces the user's skin and advanced therethrough until the exterior of delivery port 60 (FIG. 1A) or the user's skin abuts a portion of needle hub 29a and/or cartridge housing 23d. Thereafter, pen 20 can be actuated to deliver a volume of medicine, e.g., insulin, to the user.

As shown in FIGS. 4A-4C, port interface mechanism 21 may be disposed on or within cartridge housing 23d, on or within needle hub 29a of needle 29, or on or within vial body 23a of cartridge 23, respectively.

Referring in particular to FIG. 4A, in conjunction with FIGS. 3A and 3B, with port interface mechanism 21 disposed on or within cartridge housing 23d, port interface mechanism 21 may be electrically connected, e.g., via wires (not shown) or other conductive structures extending along, within, or through cartridge housing 23d to contact(s) 320 of cartridge housing 23d which, in turn, are connected with contact(s) 310 of body 20b upon engagement of cartridge housing 23d with body 20b, to thereby enable electrical communication of port interface mechanism 21 with electronics unit 27 and/or operations monitoring mechanism 28.

With reference in particular to FIG. 4B, in conjunction with FIGS. 3A and 3B, with port interface mechanism 21 disposed on or within needle hub 29a of needle 29, port interface mechanism 21 may be electrically connected to contacts 424 disposed on needle hub 29a of needle 29 which, in turn, connect with contacts 426 disposed on cartridge housing 23d upon engagement of needle hub 29a with neck 23e of vial body 23a when cartridge 23 is received within cartridge housing 23d. Contacts 426 are connected, e.g., via wires (not shown) or other conductive structures extending along, within, or through cartridge housing 23d to contact(s) 320 of cartridge housing 23d which, in turn, are connected with contact(s) 310 of body 20b upon engagement of cartridge housing 23d with body 20b, to thereby enable electrical communication of port interface mechanism 21 with electronics unit 27 and/or operations monitoring mechanism 28.

With reference in particular to FIG. 4C, with port interface mechanism 21 disposed on or within vial body 23a of cartridge 23, port interface mechanism 21 may be electrically connected to contacts 434 of via body 23a which, in turn, are electrically connected with contacts 436 of cartridge housing 23d when cartridge 23 is disposed therein. Contacts 436, in turn, are connected, e.g., via wires (not shown) or other conductive structures extending along, within, or through cartridge housing 23d to contact(s) 320 of cartridge housing 23d which, in turn, are connected with contact(s) 310 of body 20b upon engagement of cartridge housing 23d with body 20b, to thereby enable electrical communication of port interface mechanism 21 with electronics unit 27 and/or operations monitoring mechanism 28.

Turning to FIGS. 5A-6B, delivery port 60 includes a base 62 which may include an adhesive layer 63 configured to facilitate adhesion of delivery port 60 to a user's skin. Delivery port 60 further includes a dome 64 supported on base 62. Dome 64 defines an interior volume 65. A delivery cannula 66 disposed in fluid communication with interior volume 65 of dome 64 extends through base 62 and externally thereof to enable delivery cannula 66 to extend (via piercing or through a pre-defined opening) through the user's skin to a sufficient depth for delivery of medicine to the user. Dome 64 includes an entry septum 67 disposed in fluid communication with interior volume 65 and configured to receive needle 29 of pen 20 such that medicine dispensed from pen 20 is injected into interior volume 65 and, from there, through delivery cannula 66 into the user. Delivery port 60 further includes a detector mechanism 68, various configurations of which are detailed below. Detector mechanism 68 is disposed on or within delivery port 60 and may be encased in a waterproof enclosure, coating, etc. to inhibit contact with medicine, bodily fluids, etc. Additional or alternative features configured for use with delivery port 60 may be found, for example and without limitation, in U.S. Pat. Nos. 10,835,727; 8,323,250; 8,137,314; 8,226,615; and 8,277,415, the entire contents of each of which is hereby incorporated herein by reference.

Figure 6A:
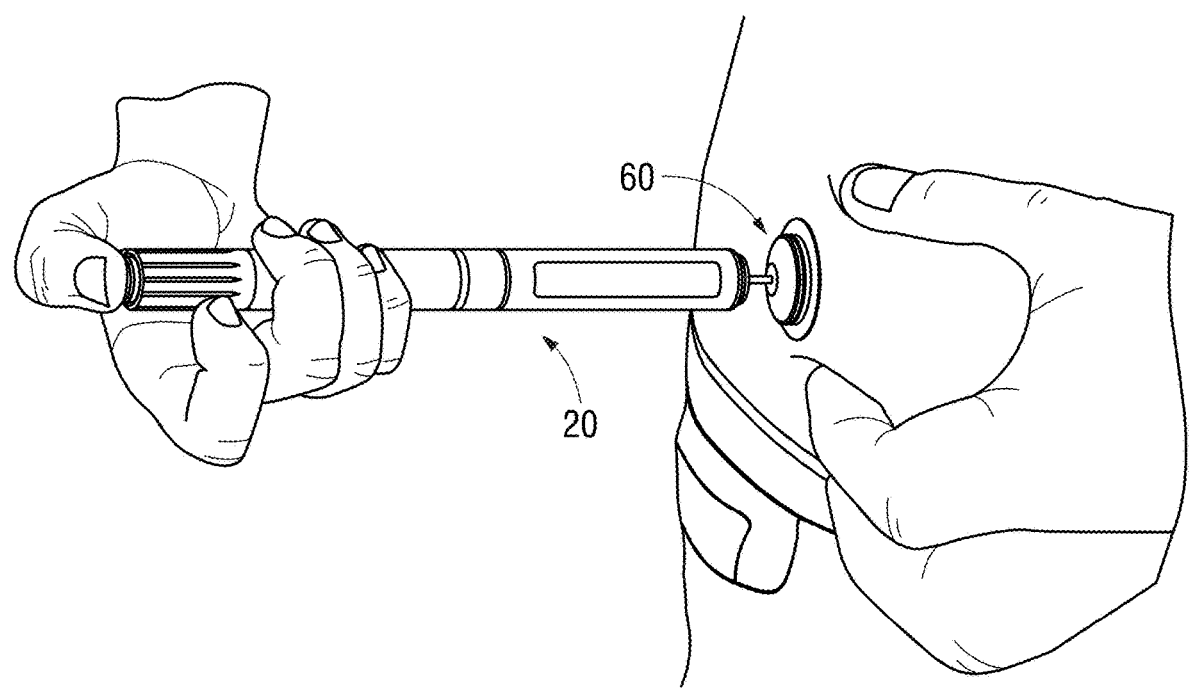
FIGS. 6A and 6B are perspective and cross-sectional views, respectively, illustrating use of the medicine injection pen and delivery port of FIG. 1A to facilitate delivery of medicine into a user.
Figure 6B:
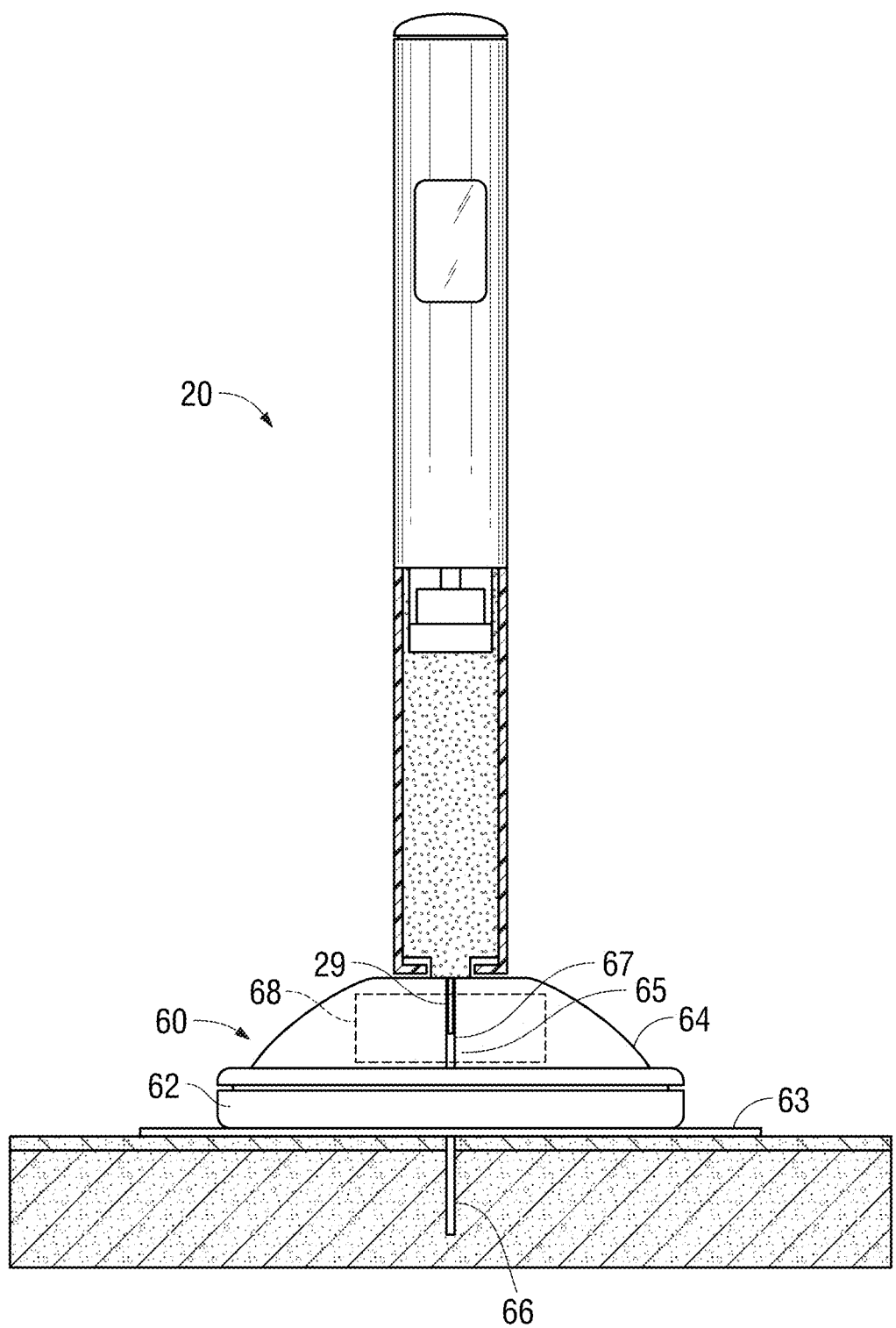

In use, as shown in FIGS. 6A and 6B, delivery port 60, if not already in position, is adhered to the user's skin with delivery cannula 66 extending through the user's skin to a sufficient depth for medicine delivery. With delivery port 60 in position, needle 29 of pen 20 is inserted through entry septum 67 of delivery port 60 and into the interior volume 65 thereof. Pen 20 may then be actuated to dispense medicine into interior volume 65, whereby as a result of pressure differentials, mechanical bias, mechanical deployment, gravity, and/or other factors, the dispensed medicine is delivered from interior volume 65 through delivery cannula 66 into the user. The mechanics, fluidics, and/or other physics of delivery port 60 may be such that the delivery of medicine to the user is achieved at a particular flow rate, throughout a particular period of time, or in accordance with any other suitable parameters or patterns. Notably, the parameters (rate, time, etc.) of delivery of medicine from delivery port 60 to the user may be similar to or different from the parameters of the dispensing of medicine from pen 20 to delivery port 60.

Figure 7:
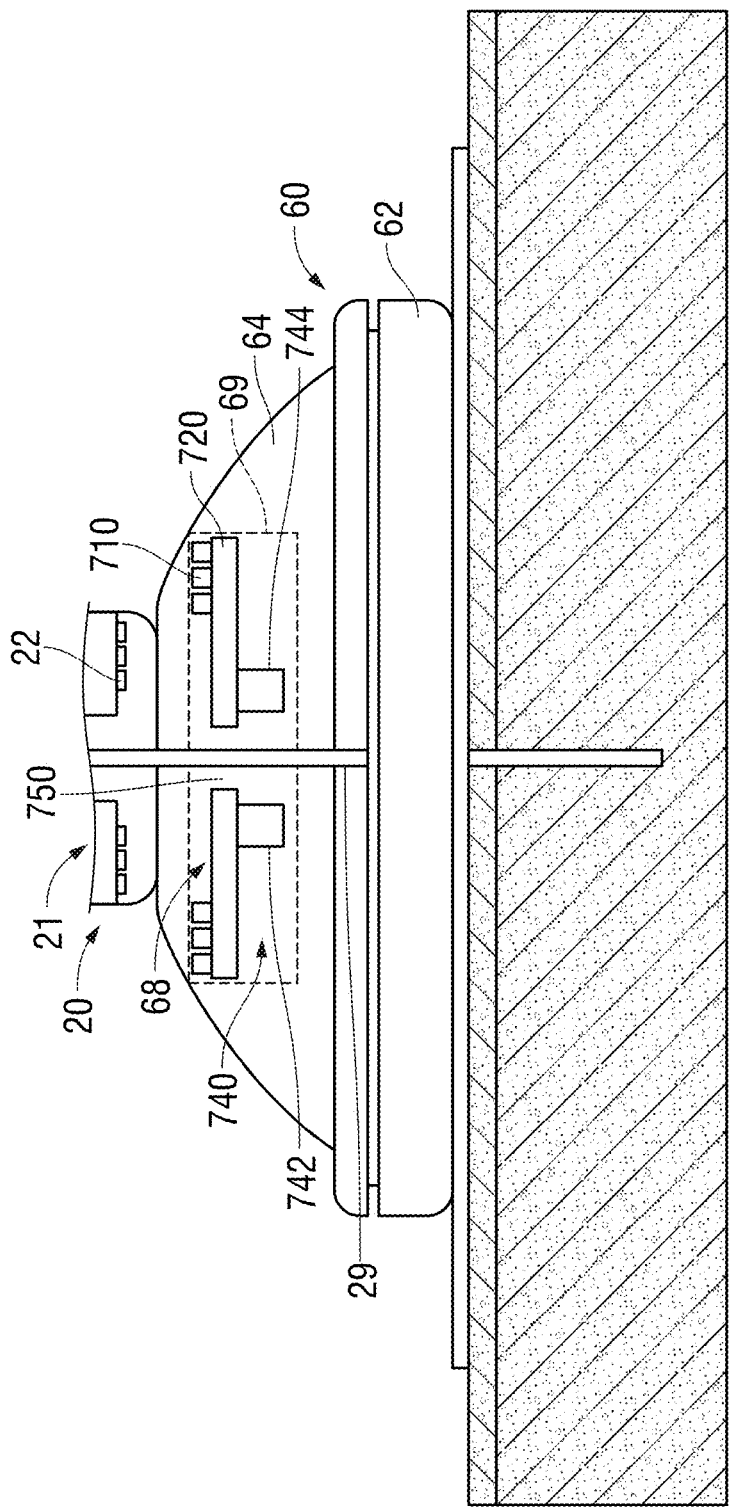
FIG. 7 is a cross-sectional view of the delivery port of FIG. 1A installed on a user with the medicine injection pen of FIG. 1A operably coupled thereto.

Referring to FIG. 7, as noted above, pen 20 includes a port interface mechanism 21 and delivery port 60 includes a detector mechanism 68. Upon sufficient approximation of pen 20 relative to delivery port 60, mechanical and/or electrical interfacing between port interface mechanism 21 and delivery port 60 is enabled; the electrical interfacing may include, for example, electrical communication of power, data, and/or control signals. To this end, port interface mechanism 21 may include, in aspects, an antenna 22 (or other suitable communication component mounted on a circuit board or otherwise configured) disposed in electrical communication with electronics unit 27, e.g., according to any of the aspects detailed above or in any other suitable manner, and configured for electrical communication with detector mechanism 68, thus enabling communication between electronics unit 27 and detector mechanism 68. Detector mechanism 68 may include, for example, an antenna 710 mounted on a circuit board 720 and configured for electrical communication with antenna 22. The communication between antenna 22 and antenna 710 may be contactless and short-range such as, for example, via NFC, RFID, or the like. Other suitable communication configurations are also contemplated. Further, it is noted that the term antenna as utilized herein is meant to encompass any wireless transmitting and/or receiving components, depending upon the particular communication configuration implemented.

With additional reference to FIGS. 8A and 8B, detector mechanism 68 includes a power storage device 730 such as, for example, a capacitor or battery, disposed on circuit board 720, e.g., on an opposite side thereof as compared to antenna 710. Detector mechanism 68 may be powered by contactless power signals communicated from antenna 22 to antenna 710, e.g., wherein such power is stored in a capacitor. In such aspects, detector mechanism 68 may be in a powered-down state in the absence of communication with antenna 22 of port interface mechanism 21 and is only woken up and activated upon establishing communication with (and receiving power signals from) antenna 22. Alternatively, where power storage device 730 of detector mechanism 68 is a battery, detector mechanism 68 may be self-powered. In such configurations, power signals communicated from antenna 22 to antenna 710 may be utilized to re-charge the battery of detector mechanism 68. Regardless of the manner in which detector mechanism 68 is powered, the powering thereof enables detector mechanism 68 to communicate with port interface mechanism 21 of pen 20. Additionally or alternatively, detector mechanism 68 may include a transmitter or transceiver (not shown) configured to enable communication of detector mechanism 68 with smartphone 30 (FIG. 1A), e.g., via WiFi, Bluetooth, cellular network, or in any other suitable manner. In aspects, the same antenna 710 enables communication to both pen 20 and smartphone 30 (FIG. 1A).

Detector mechanism 68 further includes a detector 740 that, in aspects, may be configured as an optical detector including an optical emitter 742, an optical detector 744, and a microcontroller 746 disposed on circuit board 720, e.g., on an opposite side thereof as compared to antenna 710. More specifically, circuit board 720 may define a donut-shaped configuration whereby circuit board 720 is disposed on or within delivery port 60, e.g., on or within dome 64 and/or on or within base 62, with central passage 750 through the donut-shaped circuit board 720 positioned to receive needle 29 of pen 20 therethrough when needle 29 is present on pen 20 and properly inserted into delivery port 60. Optical emitter 742 and optical detector 744 may be disposed on opposite sides of central passage 750 such that needle 29 of pen 20 interrupts or alters the optical signal transmitted therebetween when needle 29 extends through central passage 750. Thus, microcontroller 746 of detector 740 is capable of detecting whether (see FIG. 8B) or not (see FIG. 8A) needle 29 is present on pen 20 and properly inserted into delivery port 60 based upon the optical signal (or lack of optical signal) communicated from optical emitter 742 to optical detector 744. Microcontroller 746 may output a suitable communication to pen 20 (e.g., via antenna 710 and antenna 22) indicating whether or not needle 29 is present on pen 20 and properly inserted into delivery port 60. Alternatively or additionally, microcontroller 746 may output such a communication to smartphone 30.

Microcontroller 746 may store in a memory thereof, for each instance where needle 29 is detected, data indicating that a detection event occurred along with timestamp information to enable recall of previous detection events. In aspects, where multiple detection events are detected within a pre-determined time period, only a single detection event may be stored in memory to avoid double counting such as, for example, in a situation where the user inserts needle 29 only to quickly remove and re-insert needle 29. Alternatively, or additionally, microcontroller 746 may only store a detection event when needle 29 is detected for at least a pre-determined period, again to inhibit counting a detection event when need 29 is quickly inserted and removed without sufficient time to provide a dose.

In aspects, detector mechanism 68, or at least detector 740 may be encased within or otherwise sealed from the medicine within delivery port 60. For example, a housing 69 that is transparent at least in the vicinity of emitter 742 and detector 744 so as not to interfere with the optical detection may be provided to seal detector mechanism 68 or a portion thereof within delivery port 60. It is noted that housing 69 need not be rigid but, rather, may be any suitable structure and/or material that serves to seal at least a portion of detector mechanism 68 therein.

Turning to FIGS. 9A and 9B, in conjunction with FIG. 7, in other aspects, detector mechanism 68 may include a detector 940 which may be configured as an optical detector including an optical emitter 942, an optical detector 944, and a microcontroller 946 disposed on circuit board 920. Circuit board 920 may define a donut-shaped configuration whereby circuit board 920 is disposed on or within delivery port 60 with central passage 950 through the donut-shaped circuit board 920 positioned to receive needle 29 of pen 20 therethrough when needle 29 is present on pen 20 and properly inserted into delivery port 60. Optical emitter 942 and optical detector 944 may be disposed on the same side of central passage 950 and oriented towards central passage 950 such that an optical signal cannot be communicated between emitter 942 and detector 944 without needle 29 of pen 20 extending through the central passage 950 and acting as a reflector to redirect the optical signal from emitter 942 back towards detector 944. Detector 940 may otherwise be configured similar to and include any of the features of detector 740 to enable determination and communication of whether (see FIG. 9B) or not (see FIG. 9A) needle 29 is present on pen 20 and properly inserted into delivery port 60. Other suitable optical detectors for detecting the presence or absence of insertion of needle 29 of pen 20 into delivery port 60 are also contemplated.

Figure 10:
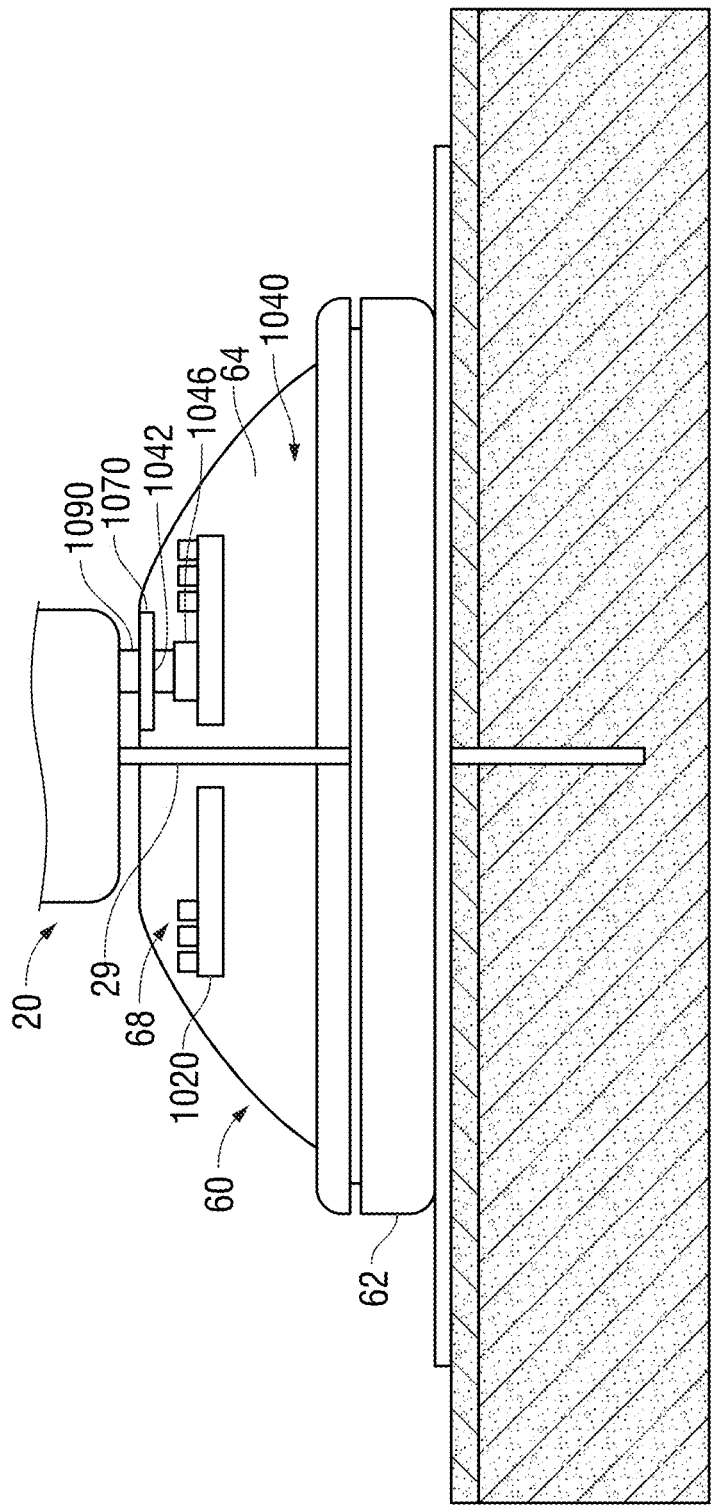
FIG. 10 is a cross-sectional view of the delivery port of FIG. 1A installed on a user with the medicine injection pen of FIG. 1A operably coupled thereto, wherein another detector module of the present disclosure is incorporated into the delivery port.

With reference to FIG. 10, in other aspects, detector mechanism 68 includes a detector 1040 which may be configured as a mechanically-actuated switch 1042 mounted on a circuit board 1020. Circuit board 1020 may be disposed on or within delivery port 60, e.g., on or within dome 64 and/or on or within base 62, and positioned such that switch 1042 is oriented towards the needle-receiving end of delivery port 60. In aspects, dome 64 of delivery port 60 includes a flexible membrane 1070 and switch 1042 is positioned within dome 64 in alignment under flexible membrane 1070 such that switch 1042 can be sealed within delivery port 60 yet still mechanically actuated from the exterior of delivery port 60, e.g., via flexion of flexible member 1070 into contact with switch 1042. Delivery port 60 may include a protrusion 1090 or other suitable feature to facilitate actuation of switch 1042 and/or pen 20 may include such a protrusion 1090 or other suitable feature.

A microcontroller 1046 of detector 1040 is capable of detecting whether or not pen 20 is properly inserted into delivery port 60 based upon whether or not switch 1042 is mechanically actuated (thereby making or breaking an underlying electrical connection within switch 1042 that is detectable by microcontroller 1046). Microcontroller 1046 may output a suitable communication to pen 20 indicating whether or not pen 20 is properly inserted into delivery port 60. Alternatively or additionally, microcontroller 1046 may output such a communication to smartphone 30. In aspects where such communication is provided to smartphone 30 (FIG. 1A), pen 20 need not be configured for communication with delivery port 60; rather, pen 20 may communicate with smartphone 30 or may be configured as a purely mechanical pen or other medicine delivery device such as a syringe.

Figure 12A:
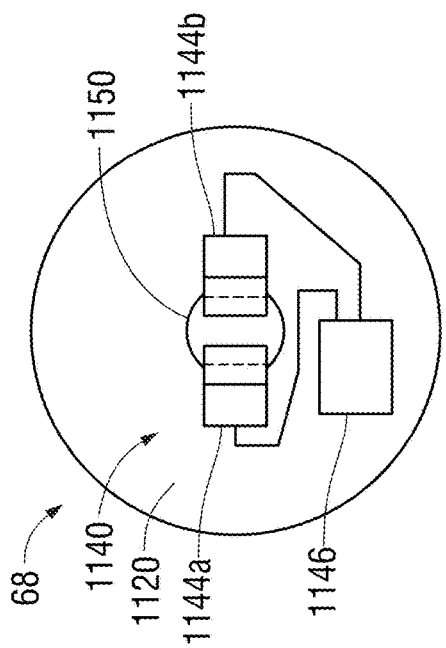
FIGS. 12A and 12B are bottom views of the detector module of FIG. 11 with and without a needle of a medicine injection device received therethrough.
Figure 12B:
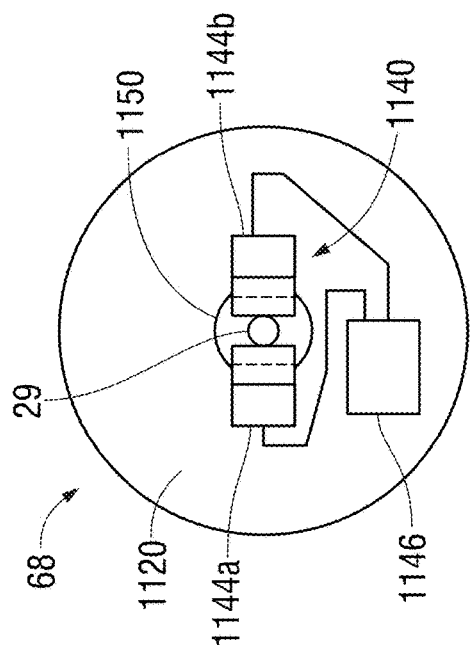
Figure 11:
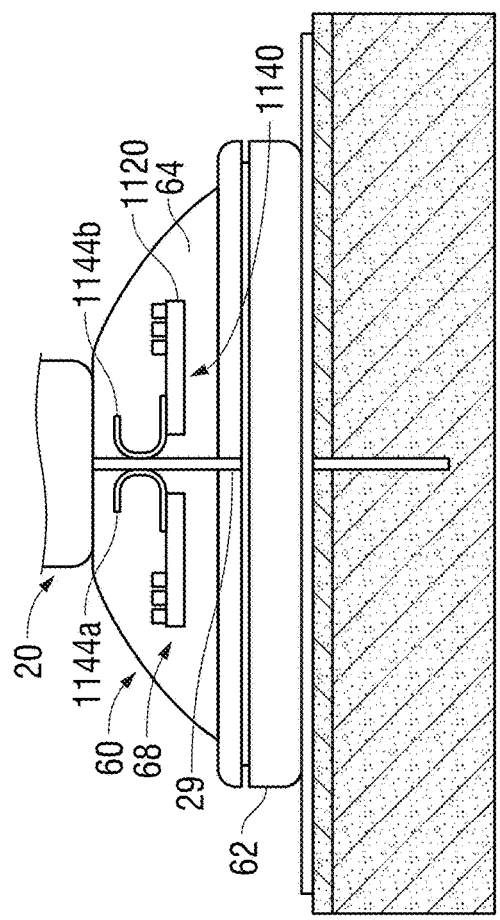
FIG. 11 is a cross-sectional view of the delivery port of FIG. 1A installed on a user with a medicine injection device such as a syringe, the medicine injection pen of FIG. 1A, or any other suitable medicine injection device operably coupled thereto, wherein another detector module of the present disclosure is incorporated into the delivery port.

Referring to FIGS. 11-12B, in still other aspects, detector mechanism 68 includes a detector 1140 that may be configured as a contact assembly including first and second contacts 1144a, 1144b mounted on a circuit board 1120. Contacts 1144a, 1144b, at rest, are spaced-apart from one another to inhibit electrical communication therebetween. In aspects, the spacing of contacts 1144a, 1144b is sufficiently large to inhibit electrical communication therebetween (absent stray currents or weak signals) but sufficiently small such that the spacing between contacts 1144a, 1144b is less than a diameter of needle 29 of pen 20. In aspects, either or both of contacts 1144a, 1144b may be configured as spring contacts, e.g., leaf spring contacts) configured to resilient flex from at-rest positions thereof.

Detector 1140 further includes a microcontroller 1146 disposed on circuit board 1120. Circuit board 1120 may define a donut-shaped configuration whereby circuit board 1120 is disposed on or within delivery port 60 with central passage 1150 through the donut-shaped circuit board 1120 positioned to receive needle 29 of pen 20 therethrough when needle 29 is present on pen 20 and properly inserted into delivery port 60. Contacts 1144a, 1144b may extend from circuit board 1120 at least partially across central passage 1150 to extend into the insertion path of needle 29 of pen 20. Thus, when needle 29 is present on pen 20 and properly inserted into delivery port 60 (e.g., along the insertion path), needle 29 makes contact with contacts 1144a, 1144b. In aspects, where at least one spring contact is provided, the contact between needle 29 and contacts 1144a, 1144b urges either or both contacts 1144a, 1144b against the bias thereof such that contacts 1144a, 1144b are maintained in contact with needle 29 under the bias thereof. Further, in aspects, contacts 1144a, 1144b define suitable features, e.g., curvatures, angles, tapers, etc., such that contacts 1144a, 1144b serve to self-center needle 29 within delivery port 60 and/or facilitate insertion of needle 29 therebetween. For example, contacts 1144a, 1144b may be configured as C-shaped contacts arranged in back-to-back orientation.

As noted above, contacts 1144a, 1144b, at rest, are spaced-apart from one another to inhibit electrical communication therebetween. However, when needle 29 is inserted therebetween and into contact therewith, the electrically-conductive, e.g., metal, needle 29 establishes electrical communication across contacts 1144a, 1144b. Contacts 1144a, 1144b are electrically connected to microcontroller 1146 such that microcontroller 1146 can detect whether electrical communication is broken or established between contacts 1144a, 1144b and, thus, whether (see FIG. 12B) or not (see FIG. 12A) needle 29 is present on pen 20 and properly inserted into delivery port 60. Microcontroller 1146 may output a suitable communication to pen 20 indicating whether or not needle 29 is present on pen 20 and properly inserted into delivery port 60. Alternatively or additionally, microcontroller 1146 may output such a communication to smartphone 30. In aspects where such communication is provided to smartphone 30, pen 20 need not be configured for communication with delivery port 60; rather, pen 20 may communicate with smartphone 30 or may be configured as a purely mechanical pen or other medicine delivery device such as a syringe.

Figure 13:
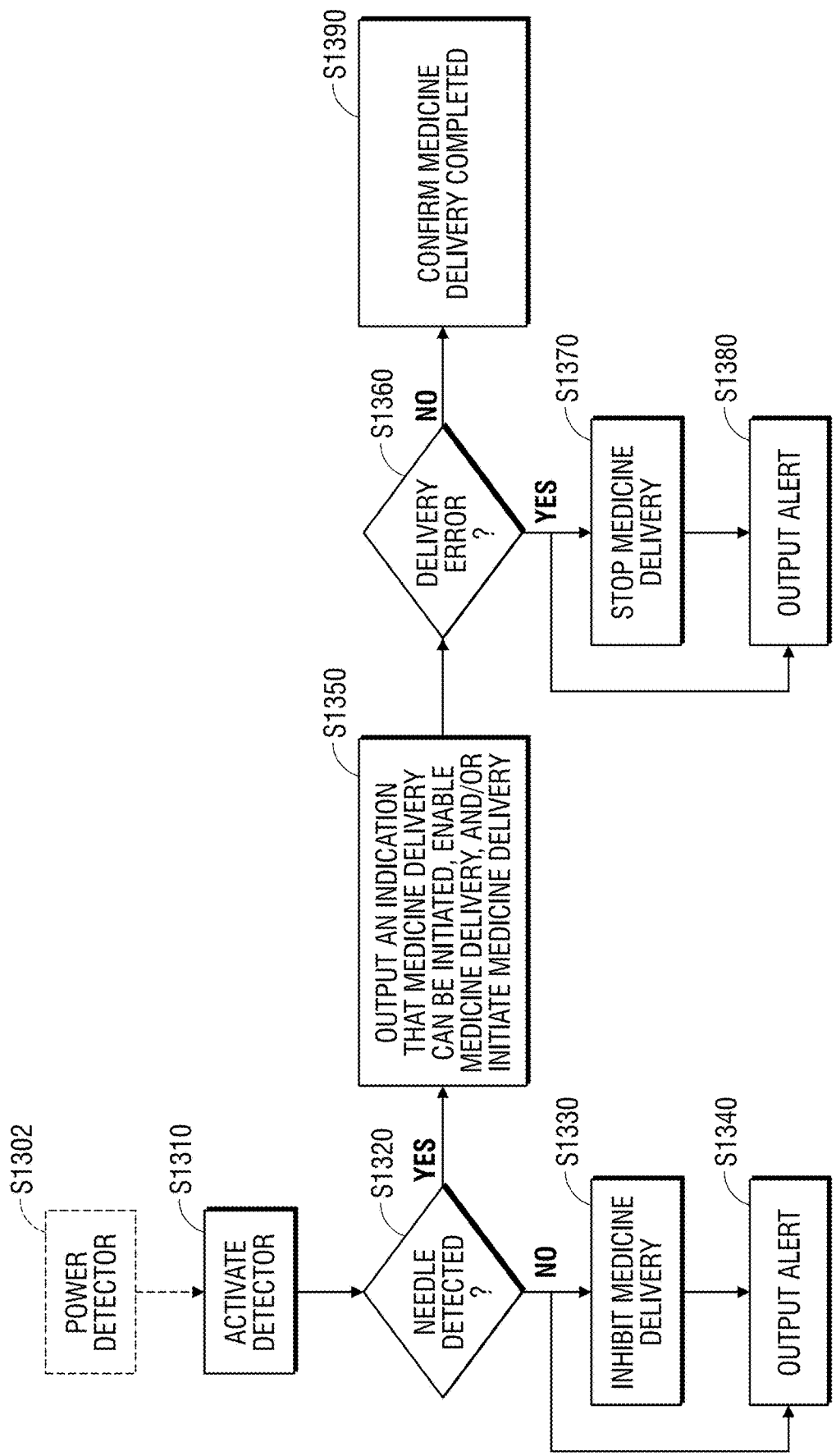
FIG. 13 is a flow diagram illustrating a method provided in accordance with aspects of the present disclosure.

With reference to FIG. 13, a method in accordance with the present disclosure to be implemented by delivery port 60 (FIGS. 5A and 5B), e.g., using any of the detectors detailed above or any other suitable detector, together with pen 20 (FIG. 1A, or other suitable medicine delivery device) and/or smartphone 30 (FIG. 1A, or other suitable connected computing device) is detailed. Initially, as indicated at step S1310, the detector of the delivery port is activated. As detailed above, and as indicated at step S1302, the detector may be powered, e.g., via pen 20 (FIG. 1A), in order to activate the detector. Alternatively, the detector may be woken up and activated based on a signal received from the pen or smartphone. Once the detector is powered, it is determined in step S1320 whether or not the needle of the pen is properly inserted into the delivery port. This may be accomplished using any one or more of the detection mechanisms detailed above or in any other suitable manner. In aspects, the needle itself is detected; in other aspects, the presence of the needle is assumed upon detection of another portion of the pen, e.g., contacting or sufficiently approximated relative to the detector.

Where it is determined that the needle is not detected, "NO" at step S1320, the method proceeds to step S1330 or S1340. More specifically, upon determining that the needle is not detected, a communication from the detector to the pen and/or smartphone signals to the pen and/or smartphone to inhibit medicine delivery, as indicated in step S1330, e.g., via activating a mechanical lockout feature preventing dose dialing and/or dose delivery. In aspects, the delivery port may include a controlled valve that can be closed (or maintained closed) when no needle is detected to thus inhibit delivery of medicine to the user. Alternatively or additionally, in step S1340, the communication from the detector to the pen and/or smartphone signals to the pen and/or smartphone to provide a suitable output alert to the user, e.g., a visual output, an audible output, a haptic output, combinations thereof, etc. In this manner, the user is alerted that there is no needle present, that the pen is not properly inserted into the delivery port, or that there is another issue that requires attention before an injection can safely be performed.

In aspects, even where the needle is detected, the method may proceed to step S1330 or 1340 after activation of the detector at step S1310 when it is determined that it is not safe to deliver medicine, e.g., insulin. For example, upon activation, the microcontroller of the detector may recall, from the memory thereof, data regarding previous detection events along with the timestamp information associated therewith. Based on this information, if the microcontroller determines that a needle was previously detected within a pre-determined time period and/or based on other factors, the method may proceed to step S1330 or S1340 to prevent or alert regarding a potential duplicate injection. Such a configuration prevents duplicate injections, including in situations where multiple medicine delivery devices are utilized. In aspects, the delivery port may include features and/or function to prevent or alert regarding a potential duplicate injection or other scenario where it is not safe for the user to dose similarly as described with respect to the accessories detailed in Patent Application Publication No. US 2020/0327973, the entire contents of which are hereby incorporated herein by reference.

Where it is determined that the needle is detected, "YES" at step S1320, indicating that the needle is installed on the pen and properly inserted into the delivery port, the method proceeds to step S1350, wherein an indication is output that the medicine delivery can be initiated, the medicine delivery is enabled (e.g., a mechanical lockout is unlocked and/or a controlled valve is opened), and/or delivery of the medicine is automatically initiated (e.g., via activation of a powered injection mechanism or release of a mechanical hold to allow for a spring-force driven injection).

During injection of the medicine from the pen into the delivery port (and, thus, to the user), it is determined at step S1360, whether an error is detected. Such an error may be identified, for example, where the detector no longer detects the needle, indicating that the pen may have been withdrawn from the delivery port prior to complete injection of the medicine. Determining whether the pen is withdrawn prematurely may be based on associating the withdrawal of the needle with, for example, information from the pen and/or smartphone indicating the amount of medicine to be delivered, feedback from the pen indicating whether or not the pen is actively dispensing medicine, detection of the needle for less than a pre-determined time, and/or other information.

As another example, an error may be detected where the detector detects the needle is present but no recorded dose is logged on the pen for a period of time, e.g., by associating the needle detection with, for example, information from the pen and/or smartphone indicating whether or not the pen is actively dispensing medicine. Detection of other errors is also contemplated, e.g., based on information from the detector of the delivery port, the smartphone, and/or the pen.

Where an error is detected, "YES" in step S1360, the method proceeds to step S1370 or S1380. More specifically, upon determining that there is an error with the medicine delivery, a communication between the detector of the delivery port, the pen, and/or the smartphone is initiated to inhibit medicine delivery, as indicated in step S1370, e.g., via activating a mechanical lockout feature, closing a controlled valve, etc. Alternatively or additionally, in step S1380, the communication may provide a suitable output alert to the user, e.g., a visual output, an audible output, a haptic output, combinations thereof, etc. to alert the user that an error has been detected.

If no error is detected, "NO" in step S1360, the method proceeds to step S1390 wherein a communication between the detector of the delivery port, the pen, and/or the smartphone is initiated to confirm that the delivery is completed. This communication may be utilized, for example, to confirm that the logged dose was delivered and may be required before the logged dose is saved, communicated, and/or utilized to update data in the system. In this manner, the dose detected by the pen can be confirmed as delivered by the delivery port before such dose information is stored and/or transmitted to the smartphone.

The various aspects and features disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described functional and/or operational aspects may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing unit" as used herein may refer to any of the foregoing structure or any other physical structure suitable for implementation of the described techniques. Also, the techniques could be fully implemented in one or more circuits or logic elements.

While several aspects of the present disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. A medicine delivery and tracking system, comprising:
   a medicine injection pen including a needle through which medicine is dispensed from the pen and an electronic unit configured to at least one of: log dispensing of medicine from the pen, control dispensing of medicine from the pen, or communicate regarding dispensing of medicine from the pen; and
   a delivery port configured for attachment to a user, the delivery port configured to receive the needle of the pen such that medicine dispensed from the pen is dispensed into the delivery port and through the delivery port to the user, wherein the delivery port includes a detector mechanism configured to detect a presence of the pen and, in response thereto, to communicate a signal to the electronic unit of the pen for use in the at least one of logging, controlling, or communicating.

2. The medicine delivery and tracking system according to claim 1, wherein the detector mechanism includes an optical detector configured to optically detect the presence of the needle of the pen within the delivery port.

3. The medicine delivery and tracking system according to claim 1, wherein the detector mechanism includes a switch configured for physical actuation by the pen to detect the presence of the pen.

4. The medicine delivery and tracking system according to claim 1, wherein the detector mechanism includes a contact assembly configured to detect the presence of the pen based on the needle of the pen establishing or breaking an electrical connection of the contact assembly.

5. The medicine delivery and tracking system according to claim 1, wherein the signal communicated from the detector mechanism of the delivery port to the electronic unit of the pen instructs the electronic unit to control the dispensing of medicine from the pen by permitting or inhibiting actuation of the pen.

6. The medicine delivery and tracking system according to claim 1, wherein the signal communicated from the detector mechanism of the delivery port to the electronic unit of the pen instructs the electronic unit to log a dispensing event only when the detector mechanism detects the presence of the pen.

7. The medicine delivery and tracking system according to claim 1, wherein the signal communicated from the detector mechanism of the delivery port to the electronic unit of the pen instructs the electronic unit to communicate an alert regarding whether dispensing of medicine from the pen is recommended or not recommended.

8. A medicine delivery and tracking system, comprising:
   a medicine injection pen including a needle through which medicine is dispensed from the pen;
   a computing device configured to at least one of: log dispensing of medicine from the pen, control dispensing of medicine from the pen, or communicate regarding dispensing of medicine from the pen; and
   a delivery port configured for attachment to a user, the delivery port configured to receive the needle of the pen such that medicine dispensed from the pen is dispensed into the delivery port and through the delivery port to the user, wherein the delivery port includes a detector mechanism configured to detect a presence of the pen and, in response thereto, to communicate a signal to the computing device for use in the at least one of logging, controlling, or communicating.

9. The medicine delivery and tracking system according to claim 8, wherein the detector mechanism includes an optical detector configured to optically detect the presence of the needle of the pen within the delivery port.

10. The medicine delivery and tracking system according to claim 8, wherein the detector mechanism includes a switch configured for physical actuation by the pen to detect the presence of the pen.

11. The medicine delivery and tracking system according to claim 8, wherein the detector mechanism includes a contact assembly configured to detect the presence of the pen based on the needle of the pen establishing or breaking an electrical connection of the contact assembly.

12. The medicine delivery and tracking system according to claim 8, wherein the signal communicated from the detector mechanism of the delivery port to the computing device instructs the computing device to control the dispensing of medicine from the pen by permitting or inhibiting actuation of the pen.

13. The medicine delivery and tracking system according to claim 8, wherein the signal communicated from the detector mechanism of the delivery port to the computing device instructs the computing device to log a dispensing event only when the detector mechanism detects the presence of the pen.

14. The medicine delivery and tracking system according to claim 8, wherein the signal communicated from the detector mechanism of the delivery port to the computing device electronic unit of the pen instructs the computing device to communicate an alert regarding whether dispensing of medicine from the pen is recommended or not recommended.

15. The medicine delivery and tracking system according to claim 8, wherein the pen includes an electronic unit configured to at least one of: log dispensing of medicine from the pen, control dispensing of medicine from the pen, or communicate regarding dispensing of medicine from the pen, and wherein the detector mechanism is configured to communicate a signal to the electronic unit of the pen for use in the at least one of logging, controlling, or communicating thereof.

* * * * *